(12) United States Patent
Asari et al.

(10) Patent No.: US 8,795,852 B2
(45) Date of Patent: Aug. 5, 2014

(54) ORGANIC ELECTROLUMINESCENT DEVICE WITH HOST MATERIALS HAVING SAME OR SIMILAR IP, EA AND T1 VALUES

(75) Inventors: Tohru Asari, Kitakyushu (JP); Hiroyuki Hayashida, Kitakyushu (JP); Kazuto Shiraishi, Kitakyushu (JP); Takayuki Shimizu, Kitakyushu (JP); Yasushi Koishikawa, Kitakyushu (JP); Kazuaki Yoshimura, Kitakyushu (JP)

(73) Assignee: Nippon Steel & Sumikin Chemical Co., Ltd., Tokyo (JP)

( * ) Notice: Subject to any disclaimer, the term of this patent is extended or adjusted under 35 U.S.C. 154(b) by 318 days.

(21) Appl. No.: 13/201,610

(22) PCT Filed: Feb. 18, 2010

(86) PCT No.: PCT/JP2010/052411
§ 371 (c)(1),
(2), (4) Date: Aug. 15, 2011

(87) PCT Pub. No.: WO2010/098246
PCT Pub. Date: Sep. 2, 2010

(65) Prior Publication Data
US 2012/0001158 A1    Jan. 5, 2012

(30) Foreign Application Priority Data
Feb. 27, 2009 (JP) .................................. 2009-046473

(51) Int. Cl.
*H01L 51/54* (2006.01)
*C09K 11/06* (2006.01)

(52) U.S. Cl.
USPC ............. 428/690; 428/917; 427/58; 313/504; 257/40; 257/E51.024

(58) Field of Classification Search
None
See application file for complete search history.

(56) References Cited

U.S. PATENT DOCUMENTS

| | | | |
|---|---|---|---|
| 2002/0163300 A1* | 11/2002 | Duineveld et al. | 313/505 |
| 2005/0069729 A1* | 3/2005 | Ueda et al. | 428/690 |
| 2008/0315753 A1* | 12/2008 | Liao et al. | 313/504 |
| 2009/0236974 A1 | 9/2009 | Tamaru et al. | |
| 2009/0295276 A1 | 12/2009 | Asari et al. | |
| 2009/0302742 A1 | 12/2009 | Komori et al. | |
| 2010/0187977 A1 | 7/2010 | Kai et al. | |

FOREIGN PATENT DOCUMENTS

| | | |
|---|---|---|
| JP | 2008-288344 A | 11/2008 |
| WO | WO 2006/112265 A1 | 10/2006 |
| WO | WO 2007/063754 A1 | 6/2007 |
| WO | WO 2007/063796 A1 | 6/2007 |
| WO | WO 2008/056746 A1 | 5/2008 |
| WO | WO 2008/149691 A1 | 11/2008 |
| WO | WO 2008/146839 A1 | 12/2008 |

OTHER PUBLICATIONS

International Search Report, dated May 25, 2010 for PCT/JP2010/052411.
International Preliminary Report on Patentability issued Oct. 27, 2011, in PCT International Application No. PCT/JP2010/052411.

* cited by examiner

*Primary Examiner* — Andrew K Bohaty
(74) *Attorney, Agent, or Firm* — Birch, Stewart, Kolasch & Birch, LLP

(57) ABSTRACT

Disclosed is a highly reliable organic electroluminescent device, in particular, a phosphorescent organic electroluminescent device using a low-molecular-weight host material, wherein a good balance between electron and hole injection and an efficient mechanism of phosphorescence are maintained. The organic electroluminescent device contains a light-emitting layer between an anode layer and a cathode layer and the light-emitting layer comprises a phosphorescent dopant material and a host material with a molecular weight of not more than 10,000. The host material is composed of a first host material and a second host material that is different from the first host material and the first host material differs from the second host material by not more than 0.1 eV in the ionization potential (IP), by not more than 0.1 eV in the electron affinity (EA), and by not more than 0.1 eV in the triplet energy (T1).

6 Claims, 1 Drawing Sheet

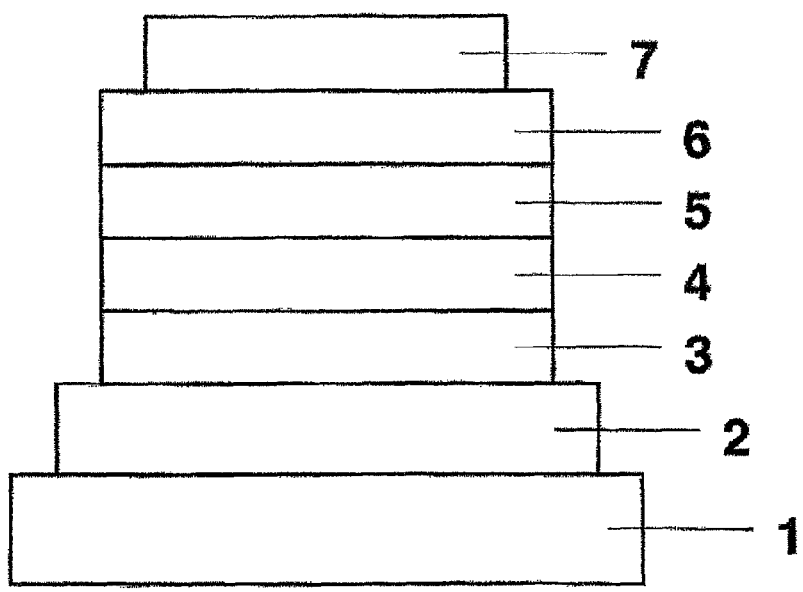

ORGANIC ELECTROLUMINESCENT DEVICE WITH HOST MATERIALS HAVING SAME OR SIMILAR IP, EA AND T1 VALUES

FIELD OF TECHNOLOGY

This invention relates to an organic electroluminescent device which displays high luminance by simultaneous use of a phosphorescent dopant material and a host material.

BACKGROUND TECHNOLOGY

An organic electroluminescent device (organic EL device) in the simplest structure is constituted of a light-emitting layer and a pair of counter electrodes sandwiching the said light-emitting layer. The device functions by utilizing the following phenomenon: upon application of an electrical field between the electrodes, electrons injected from the cathode and holes injected from the anode recombine in the light-emitting layer to generate excitons and the energy level of the excitons returns from the conduction band to the valence band with release of energy as light.

Organic EL devices are classified into fluorescent organic EL devices and phosphorescent EL devices by the mechanism of emission of light. The light-emitting layer of a phosphorescent organic EL device is generally composed of a phosphorescent dopant material and a host material. Utilization of a phosphorescent dopant material in emission of light is equivalent to utilization of triplet excitons that are generated with 75% probability; hence, it is likely that a phosphorescent organic EL device is capable of performing at higher luminous efficiency than a fluorescent organic EL device utilizing singlet excitons that are generated with 25% probability.

In recent years, in the field of phosphorescent organic EL devices with a potentiality to attain the aforementioned high luminous efficiency, researches and developmental works are directed toward the use of low-molecular-weight compounds as host materials in the light-emitting layer. One of the main reasons for this trend is that low-molecular-weight compounds to be used as host materials are obtained readily in high purity by such purification techniques as sublimation, column chromatography, and recrystallization. Raising the purity of a low-molecular-weight host material reduces the number of energy trap sites derived from the impurities and minimizes thermal deactivation of electrons and holes injected from the electrodes or of excitons and, as a result, higher purity helps to provide a device of higher performance. On the other hand, low-molecular-weight compounds exhibit the characteristic property common to them that the crystallinity becomes increasingly higher as the purity is raised. In consequence, there may arise a problem that a high-purity low-molecular-weight host material incorporated in the light-emitting layer of a device may partly crystallize in fine crystals by the action of feeble heat generated while the device is in operation and harms the amorphous property of the light-emitting layer to eventually degrade the quality of the device. This special property exerts a profound influence when a film constituting the light-emitting layer is made by a wet process. The plausible explanation is that, in making a film by a wet process, a solution of a low-molecular-weight host compound is applied and the solvent is then evaporated off in the drying step where the solution temporarily becomes highly concentrated or the solution goes through a condition that favors crystallization. This fact presents the largest problem that a low-molecular-weight host material, although it displays high performance in film forming by the vapor deposition process, is not applicable to film forming by a wet process.

To solve the aforementioned problems, a number of methods have been disclosed for securing the stability of the light-emitting layer in the amorphous state by mixing at least another low-molecular-weight host material into the base low-molecular-weight host material. For example, mixing of an amorphous polymeric material is disclosed in patent document 1 and mixing of electrical charge-injecting and electrical charge-transporting auxiliaries is disclosed in patent documents 2-6.

PRIOR-ART TECHNICAL DOCUMENTS

Patent Documents

Patent document 1: JP2002-203674 A
Patent document 2: JP H11-354279 A
Patent document 3: JP2003-068466 A
Patent document 4: JP2004-335204 A
Patent document 5: JP2006-135295 A
Patent document 6: JP2006-148045 A However, the aforementioned methods have problems in that the first host material differs from the second host material in molecular parameters such as the ionization potential (hereinafter referred to as IP), the electron affinity (hereinafter referred to as EA), and the triplet excitation energy level (hereinafter referred to as T1) and mixing of the second host material into the first host material degrades the characteristics of the device, for example, by causing large changes in the injected amount of electrons holes or by failing to maintain the original color of emitted light when the second host material has a low value of T1.

SUMMARY OF THE INVENTION

An object of this invention is to provide a low-molecular-weight host material for an organic electroluminescent device which can be formed into a film by a wet process with inhibition of crystallization so that a device in which the low-molecular-weight host material is incorporated can maintain a good balance of injected electrons and holes as well as an efficient mechanism of phosphorescence by inhibiting crystallization of the material by the action of feeble heat generated while the device is in operation and to provide a highly reliable phosphorescent organic electroluminescent device.

This invention relates to an organic electroluminescent device containing a light-emitting layer formed by a wet process between an anode and a cathode wherein the light-emitting layer comprises a phosphorescent dopant material and a host material having a molecular weight of not more than 10,000, the said host material is composed of a first host material and a second host material that is different from the first host material, the ratio by weight of the first host material to the second host material is 90/10 to 10/90, and the first host material differs from the second host material by not more than 0.1 eV in the ionization potential (IP), by not more than 0.1 eV in the electron affinity (EA), and by not more than 0.1 eV in the triplet excitation energy (T1).

A preferable compound for the aforementioned first host material or second host material is a heterocyclic compound selected from the group consisting of indolocarbazole derivatives and triazine derivatives.

The aforementioned heterocyclic compound is represented by the following formula (1).

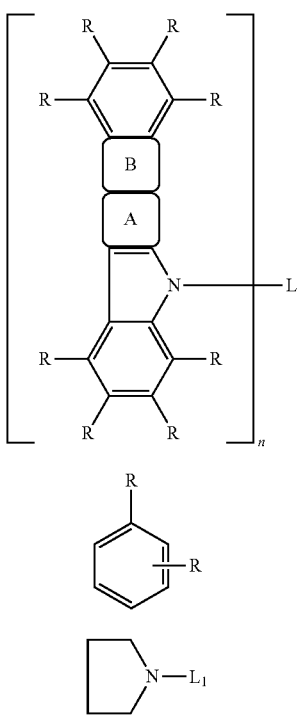

(1)

(1a)

(1b)

In formula (1), ring A is an aromatic ring represented by formula (1a) and is fused to the adjacent rings at arbitrary positions and ring B is a heterocycle represented by formula (1b) and is fused to the adjacent rings at arbitrary positions; R in formulas (1) and (1a) is independently hydrogen or a monovalent substituent and the adjacent substituents may together form a ring; $L_1$ in formula (1b) is independently an aromatic hydrocarbon group or an aromatic heterocyclic group; L is an n-valent aromatic hydrocarbon group or an n-valent aromatic heterocyclic group; n is 1-4 and, when n is 2 or more, the fused heterocycle containing rings A and B may be identical with or different from one another.

Preferable examples of the heterocyclic compounds for the first host material or the second host material are represented by the following formula (2) or (3).

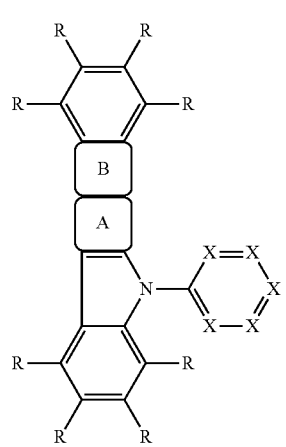

(2)

In formula (2), ring A, ring B, and R respectively have the same meaning as in formula (1); X is independently C—H, N, C-$L_2$, and $L_2$ is independently an aromatic hydrocarbon group or an aromatic heterocyclic group.

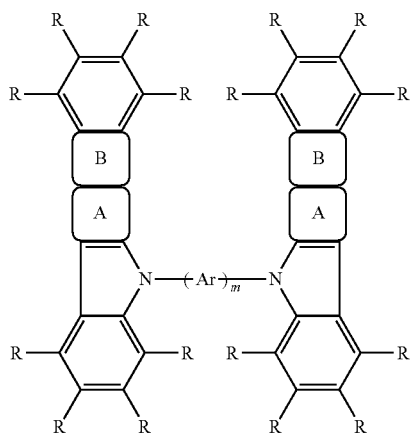

(3)

In formula (3), ring A, ring B, and R respectively have the same meaning as in formula (1) and the fused heterocycle containing rings A and B may be identical with or different from each other; Ar is independently a phenylene group or a divalent aromatic heterocyclic group; m is 1-5.

Further, this invention relates to an organic electroluminescent device wherein the first host material and the second host material are two species of heterocyclic compounds selected from the heterocyclic compounds represented by formula (2) or (3).

The ratio by weight of the first host material to the second host material is preferably 75/25 to 25/75.

BRIEF DESCRIPTION OF THE DRAWING

FIG. 1 is a schematic drawing of an example of an organic EL device according to this invention.

PREFERRED EMBODIMENTS OF THE INVENTION

An organic EL device in this invention contains an anode (or an anode layer), a cathode (or a cathode layer), and organic layers sandwiched between the anode and the cathode. At least one of the organic layers is a light-emitting layer. The layered structure of the device is not specifically restricted and a typical structure is the one illustrated in FIG. 1. An organic EL device in this invention contains a substrate 1, an anode 2, a light-emitting layer 5, and a cathode 7 as essential layers and other layers may be provided according to the need to improve the performance of the device. The organic EL device illustrated in FIG. 1 contains layers piled one upon another in the order of the substrate 1, the anode 2, a hole-injecting layer 3, a hole-transporting layer 4, the light-emitting layer 5, an electron-transporting layer 6, and the cathode 7; however, it is allowable to omit the non-essential layers or to add or replace with layers other than the aforementioned ones according to the need.

The light-emitting layer of an organic EL device in this invention comprises a phosphorescent dopant material and a host material having a molecular weight of not more than 10,000 and the host material is composed of a first host material and a second host material. The second host material is at least one species of host material that is different from the first host material. For the sake of convenience in explanation, a host material selected first is referred to as the first host material and another host material different therefrom is referred to as the second host material. The second host material may contain two species or more of compounds, but preferably it consists of one species. In the case where the second host material contains two species or more of compounds, each of them satisfies the requirements for IP, EA, and T1 to be described below in relation to the first host material.

The second host material is effective for inhibiting crystallization of the first host material. A device displaying a high degree of luminance contains a host material whose IP, EA, and T1 are already controlled at proper values. Therefore, it is desirable from the viewpoint of retaining high luminance that the values of IP, EA, and T1 of another host material to be mixed are the same as those of the host material already incorporated. Since the values of these factors are characteristic of a given molecule and calculated from its molecular structure, no two compounds existing in reality show identical values of the three factors. However, it has been found that a device of high luminance in which the first host material and the second host material differ from each other by not more than 0.10 eV in each of IP, EA, and T1 is able to inhibit crystallization of the light-emitting layer and maintain good luminous characteristics over a prolonged period of time while maintaining high luminance.

The values of IP and EA of a host material, either a first host material or a second host material, are characteristic of a compound to be used as such and are respectively equal to the negative of the HOMO energy and the LUMO energy calculated on the basis of the molecular structure. This relationship is defined as Koopmans' theorem in the restricted Hartree-Fock theory or as Janak's theorem in the density functional theory (DFT). For example, the values of the HOMO energy and the LUMO energy, respectively in terms of eV unit, can be calculated by DFT structure optimization using the molecular orbital program Gaussian 03, rev. CO2. Further, the value of T1 is equal to the lowest value of the triplet excitation energy calculated as a value characteristic of a compound to be used as a host material on the basis of the molecular structure. The triplet excitation energy is calculated, for example, by DFT structure optimization followed by time-dependent DFT (TD-DFT) calculation on the basis of the optimized structure using the molecular orbital program Gaussian 03, rev. CO2. There is no specific restriction on the method for calculating IP, EA, and T1 in this invention; however, the same method is used in calculating the values for a first host material and a second host material to avoid errors due to the use of different methods of calculation.

Compounds to be used as the first host material or the second host material are not specifically limited as long as they are applicable to organic EL devices as host materials and they are low-molecular-weight compounds having a molecular weight of not more than 10,000, preferably 500-5,000. Compounds useful for host materials are published in a large number of patent documents and elsewhere and a selection may be made from them.

Compounds suitable for use as the first host material or the second host material are heterocyclic compounds having an electron transport property such as heterocyclic compounds containing a carbazolyl group, an indolobarbazolyl group, an oxadiazolyl group, or a triazinyl group; preferably, heterocyclic compounds selected from the group consisting of indolocarbazole derivatives and triazine derivatives. Here, the indolocarbazole derivatives refer to those compounds which have an indolocarbazole skeleton and they may have one or more substituents. Preferable substituents are those containing a triazine ring. The triazine derivatives refer to compounds containing a triazine ring and they may have one or more substituents. Indolocarbazole derivatives having a triazine ring as a substituent are triazine derivatives in a sense.

The heterocyclic compounds represented preferably by the aforementioned formula (1), more preferably by formula (2) or (3), are suitable for use as the first host material or the second host material. In formula (1), (2), or (3), ring A is an aromatic ring represented by formula (1a) and ring B is a heterocycle represented by formula (1b). Supposing that the three-membered fused ring composed of ring A and the indole ring underneath ring A is a carbazole ring, the fusion of ring B to the adjacent carbazole ring may occur between the 2,3-position or the 4,5-position of ring B (numbering starts from N as position 1) and the 1,2-, 2,3-, or 3,4-position of the carbazole ring and ring B may be fused in two ways, namely, it is fused as it is or it is overturned and then fused. In consequence, there exist five isomers for the fused heterocycle containing ring A and ring B in formula (1), (2), or (3) and all of these fused heterocycles are indolocarbazole rings.

In formula (1), L is an n-valent aromatic hydrocarbon group or an n-valent aromatic heterocyclic group, preferably an n-valent aromatic hydrocarbon group of 6-100 carbon atoms or an n-valent aromatic heterocyclic group of 3-100 carbon atoms, more preferably an n-valent aromatic hydrocarbon group of 6-36 carbon atoms or an n-valent aromatic heterocyclic group of 3-35 carbon atoms. The aromatic hydrocarbon groups or aromatic heterocyclic groups may have substituents; in the case where there are two or more substituents, they may be identical with or different from one another. In counting the total number of carbon atoms, the number of carbon atoms in the substituents is included.

Preferable examples of the aromatic hydrocarbon groups and aromatic heterocyclic groups include the groups formed by removing n hydrogen atoms from the aromatic compounds enumerated below: benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene, pyranthrene, ovalene, corannulene, fulminene, anthanthrene, zethrene, terrylene, naphthacenonaphthalene, truxene, furan, benzofuran, isobenzofuran, xanthenes, oxanthrene, dibenzofuran, perixanthenoxanthene, thiophene, thioxanthene, thianthrene, phenoxathiin, thionaphthene, isothianaphthene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, carbazole, indolocarbazole, imidazole, naphthyridne, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, thebenidine, quindoline, quinindoline, acrindoline, phthaloperine, triphenodithiazine, triphenodioxazine, phenanthrazine, anthrazine, benzothiazole, benzimidazole, benzoxazole, benzisoxazole, and benzisothiazole. More preferable examples include the groups similarly formed by removing n hydrogen atoms from benzene, pyridine, pyrazine, pyrimidine, pyridazine, triazine, indole, and carbazole. Preferable examples further include the groups formed by removing n hydrogen atoms from the aromatic compounds that are formed by linking a plurality of the compounds enumerated above. More preferable examples include the groups formed by removing n hydrogen atoms from bezene, pyridine, pyrazine, pyrimidine, pyridazine, triazine, indole, and carbazole or from aromatic compounds formed by linking a plurality thereof. In the case where the groups are derived from the aromatic compounds formed by linking a plurality of aromatic rings, the number of aromatic rings to be linked is preferably 2-10, more preferably 2-5, and the aromatic rings to be linked may be identical with or different from one another. In this case, there is no restriction where the linkage of the aromatic compound composed of a plurality of linked rings occurs to the nitrogen atom of the indolocarbazole ring containing rings A and B and it may occur either at a ring located at the end or in the middle of the linked aromatic rings. Further, in the case where an aromatic heterocycle is included in the linked aromatic rings, such a group is included in the aromatic heterocyclic groups. Here, the aromatic ring is used as a general term for an aromatic hydrocarbon ring and an aromatic heterocycle.

The groups formed by linking a plurality of aromatic rings may be expressed by the following formulas when n=1.

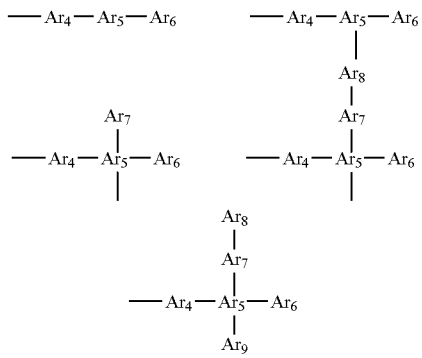

(Each of $Ar_4$ to $Ar_9$ is a substituted or unsubstituted aromatic ring.)

Examples of the aforementioned groups formed by linking a plurality of aromatic rings include the groups formed by removing n hydrogen atoms from biphenyl, terphenyl, bipyridine, bipyrimidine, bitriazine, terpyridine, bistriazylbenzene, dicarbazolylbenzene, carbazolylbiphenyl, dicarbazolylbiphenyl, phenylterphenyl, carbazolylterphenyl, binaphthalene, phenylpyridine, phenylcarbazole, diphenylcarbazole, diphenylpyridine, phenylpyrimidine, diphenylpyrimidine, phenyltriazine, diphenyltriazine, phenylnaphthalene, diphenylnaphthalene, indolocarbazolylbenzene, indolocarbazolylpyridine, and indolocarbazolyltriazine. Preferable examples include the groups formed by removing n hydrogen atoms from aromatic compounds formed by linking aromatic compounds selected from benzene, pyridine, pyrazine, pyrimidine, pyridazine, triazine, indole, and carbazole.

In the case where the aforementioned aromatic hydrocarbon groups or aromatic heterocyclic groups have substituents, the total number of substituents is 1-10, preferably 1-6, more preferably 1-4. Likewise, the groups derived from the aromatic compounds that are formed by linking a plurality of aromatic rings may have substituents. Preferable examples of such substituents include an alkyl group of 1-20 carbon atoms, an alkoxyl group of 1-20 carbon atoms, an alkylthio group of 1-20 carbon atoms, an alkyl-substituted amino group of 1-20 carbon atoms, an acyl group of 2-20 carbon atoms, a diarylamino group of 12-24 carbon atoms, an alkenyl group of 2-10 carbon atoms, an alkynyl group of 2-10 carbon atoms, an alkoxycarbonyl group of 2-10 carbon atoms, an alkylsulfonyl group of 1-10 carbon atoms, a haloalkyl group of 1-10 carbon atoms, an amide group, an alkylamide group of 2-10 carbon atoms, a trialkylsilyl group of 3-20 carbon atoms, a trialkylsilylalkyl group of 4-20 carbon atoms, a trialkylsilylalkenyl group of 5-20 carbon atoms, a trialkylsilylalkynyl group of 5-20 carbon atoms, a cyano group, a nitro group, and a hydroxyl group. More preferable examples include a methyl group, an ethyl group, an n-propyl group, an isopropyl group, an n-butyl group, a tert-butyl group, a methoxy group, an ethoxy group, an n-propoxy group, an isopropoxy group, and a diphenylamino group.

In formula (1), n is 1-4, preferably 1 or 2.

In formula (1b), $L_1$ is independently an aromatic hydrocarbon group or an aromatic heterocyclic group and explanation of L (when n=1) in the aforementioned formula (1) holds true here. Likewise, in the case where $L_1$ has substituents, explanation of the substituents of L in the aforementioned formula (1) holds true here.

In formulas (1) and (1a), R is independently hydrogen or a monovalent substituent. In the case where R is a monovalent substituent, examples include an aromatic hydrocarbon group of 6-26 carbon atoms, an aromatic heterocyclic group of 3-25 carbon atoms, an alkyl group of 1-20 carbon atoms, an alkoxyl group of 1-20 carbon atoms, an alkylthio group of 1-20 carbon atoms, an alkyl-substituted amino group of 1-20 carbon atoms, an acyl group of 2-20 carbon atoms, a diarylamino group of 12-24 carbon atoms, an alkenyl group of 2-10 carbon atoms, an alkynyl group of 2-10 carbon atoms, an alkoxycarbonyl group of 2-10 carbon atoms, an alkylsulfonyl group of 1-10 carbon atoms, a haloalkyl group of 1-10 carbon atoms, an amide group, an alkylamide group of 2-10 carbon atoms, a trialkylsilyl group of 3-20 carbon atoms, a trialkylsilylalkyl group of 4-20 carbon atoms, a trialkylsilylalkenyl group of 5-20 carbon atoms, a trialkylsilylalkynyl group of 5-20 carbon atoms, a cyano group, a nitro group, and a hydroxyl group. Preferable examples include an aromatic hydrocarbon group of 6-26 carbon atoms, an aromatic heterocyclic group of 3-25 carbon atoms, an alkyl group of 1-20 carbon atoms, an alkoxyl group of 1-20 carbon atoms, and a diarylamino group of 12-24 carbon atoms; concretely, they include a phenyl group, a pyridyl group, a pyrimidyl group, a triazyl group, an indolyl group, a carbazolyl group, a methyl group, an ethyl group, an n-propyl group, an isopropyl group, an n-butyl-group, a tert-butyl group, a methoxy group, an ethoxy group, an n-propoxy group, an isopropxy group, and a diphenylamino group. In the case where a plurality of Rs are present, they may be identical with or different from one another.

In formulas (2) and (3), ring A, ring B, and R respectively have the same meaning as in formula (1). In formula (2), X is independently N, C—H, or C-$L_2$ and the number of Ns is 1-3, preferably 2-3, more preferably 3.

In the case where X in formula (2) is C-$L_2$, $L_2$ is independently an aromatic hydrocarbon group or an aromatic heterocyclic group. Preferable examples of $L_2$ are the same as the aromatic hydrocarbon groups or aromatic heterocyclic groups cited in explanation of L in the aforementioned formula (1) where n=1. When $L_2$ is an aromatic hydrocarbon group or aromatic heterocyclic group having substituents, the substituents are the same as those of L in formula (1) explained on that occasion.

In formula (3), Ar is independently a phenylene group or a divalent aromatic heterocyclic group, preferably the groups formed by removing two hydrogen atoms from benzene, pyridine, pyrimidine, triazine, indole, and carbazole. In the case where Ar has substituents, the substituents are the same as R in formula (1) and (1a) in the case where R is a monovalent substituent. The symbol m is the number of repeating and it is 1-5, preferably 1-3. When m is 2 or more, Ars may be identical with or different from one another.

Concrete examples of the compounds represented by formulas (1)-(3) are shown below, but they are not limited thereto. The number assigned to the chemical formula is the compound number.

The compounds represented by formula (1) are illustrated below.

1-1

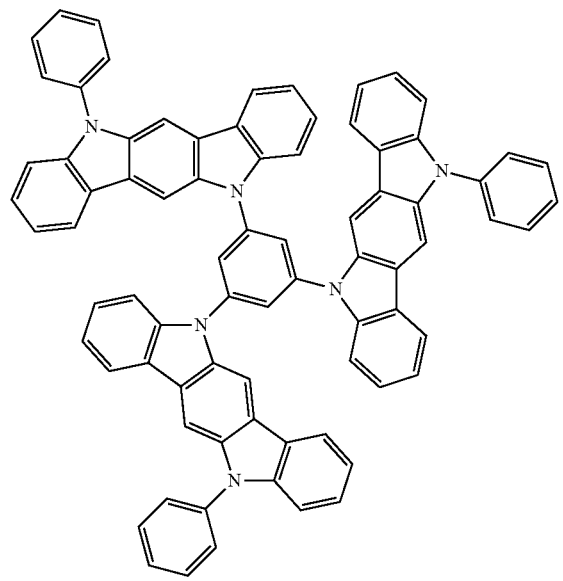

1-2

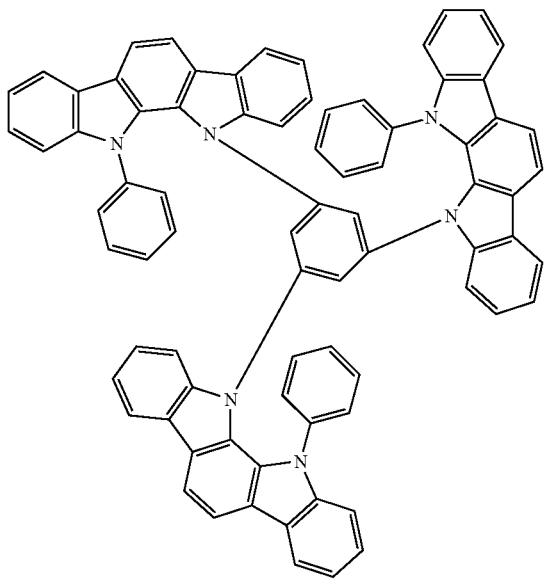

1-3

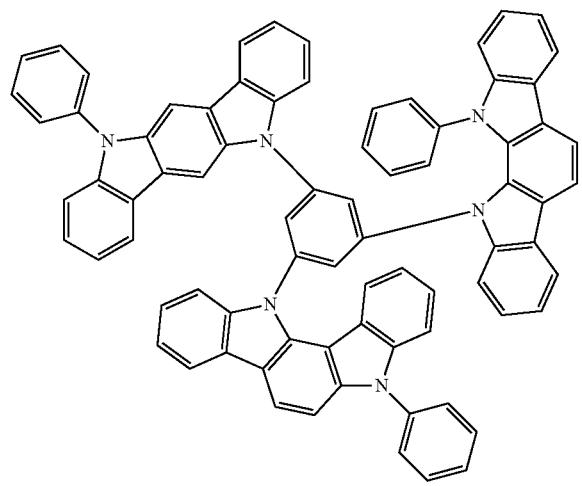

1-4

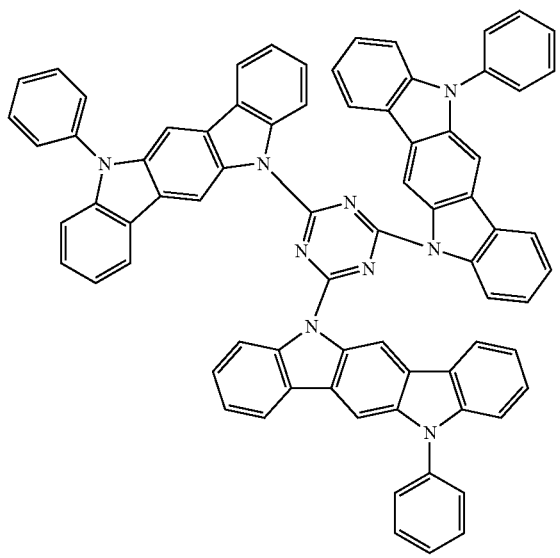

-continued
1-5
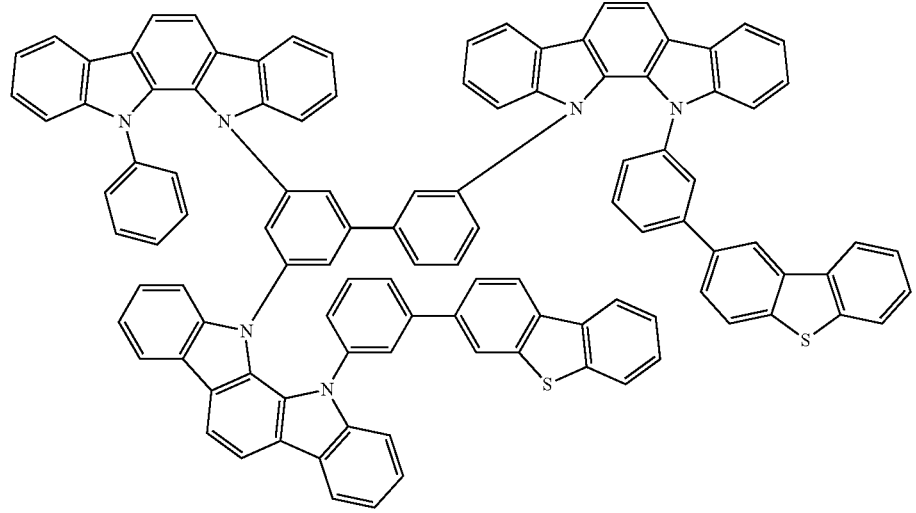
1-6
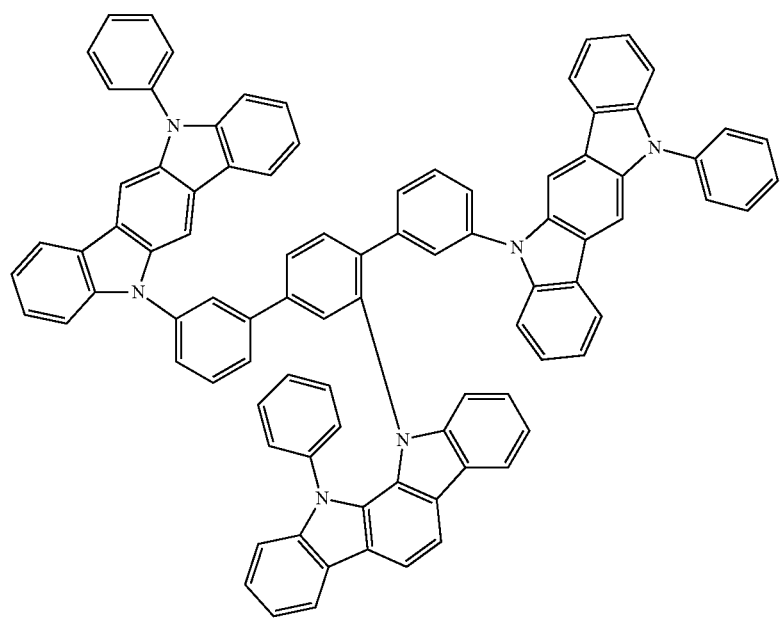

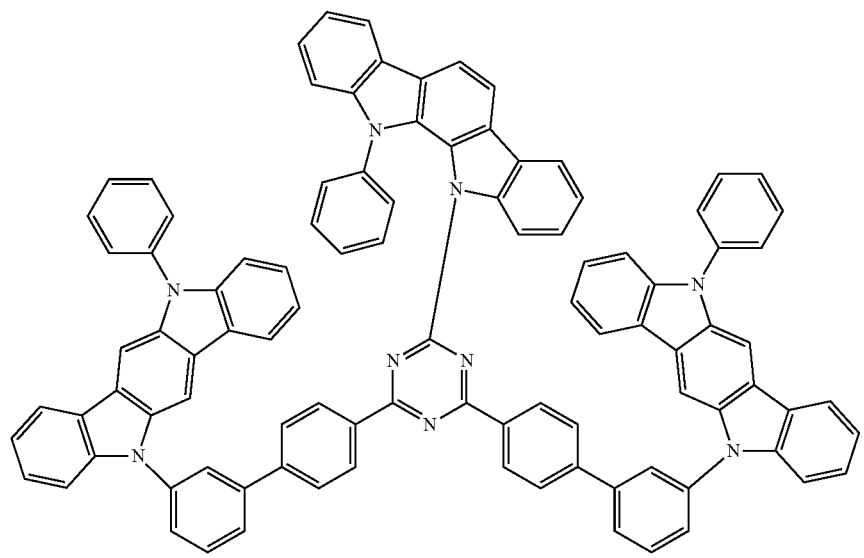
1-7
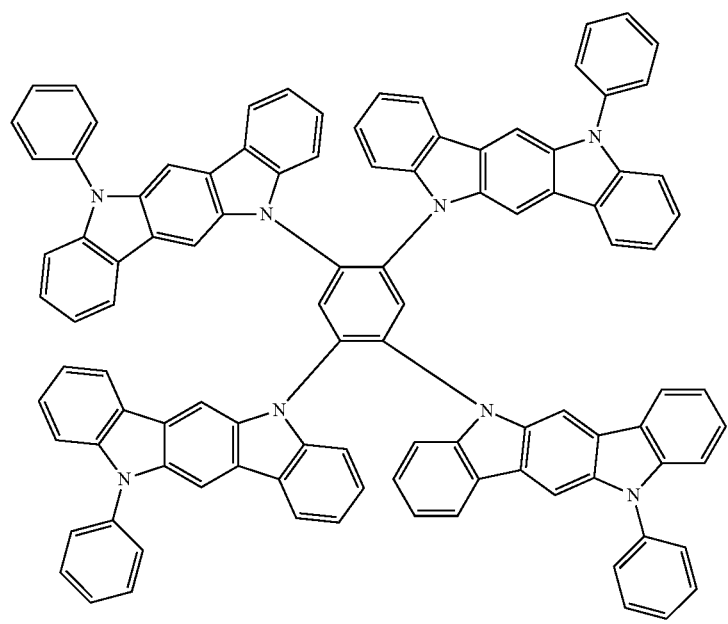
1-8

-continued
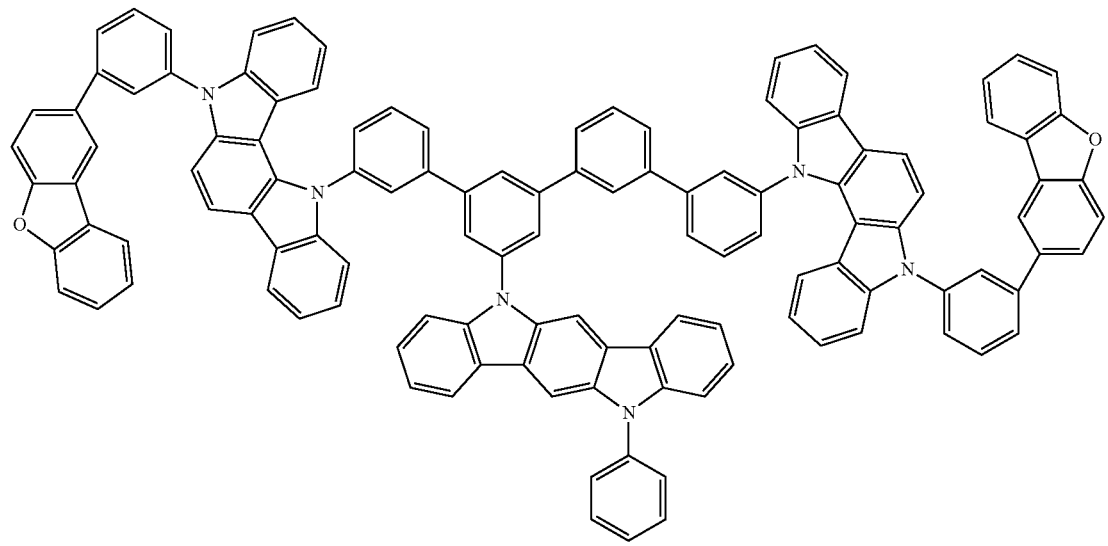
1-9
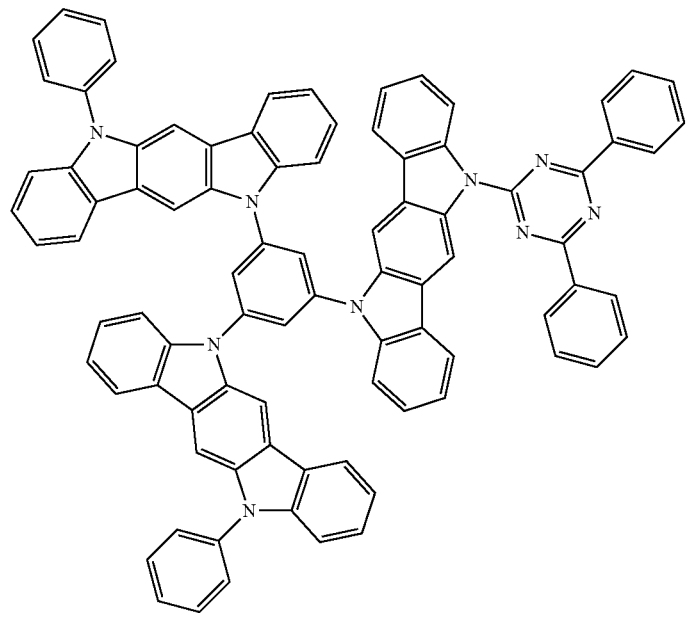
1-10
The compounds represented by formula (2) are illustrated below.
-continued
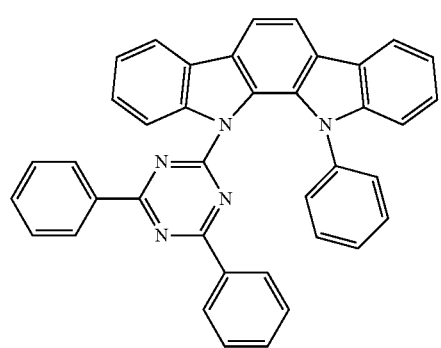
2-1
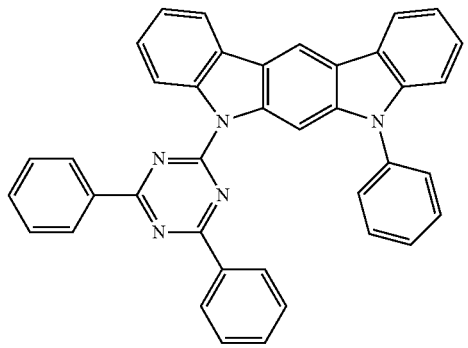
2-2

2-3
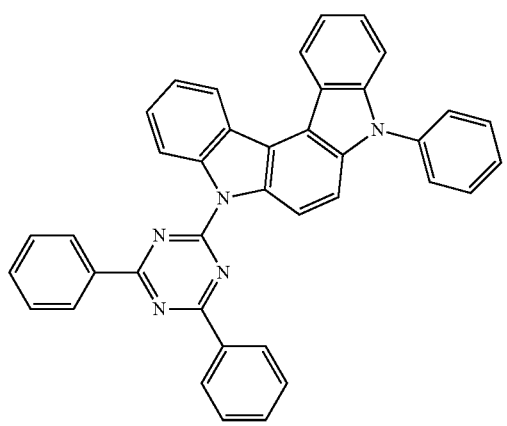
2-4
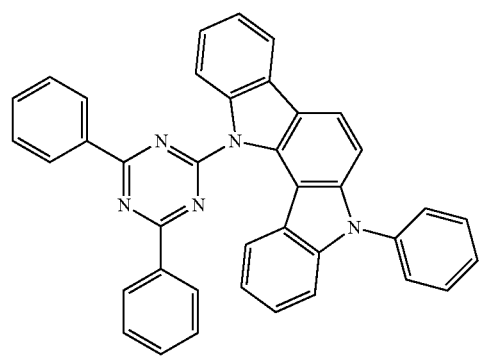
2-5
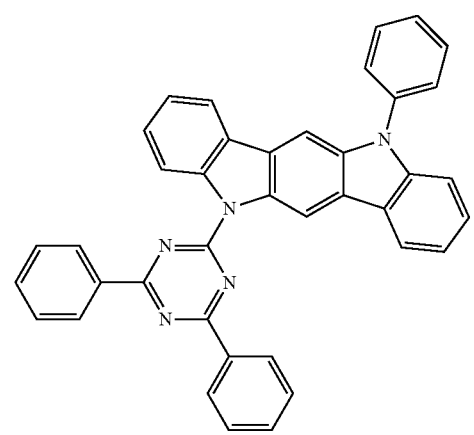
2-6
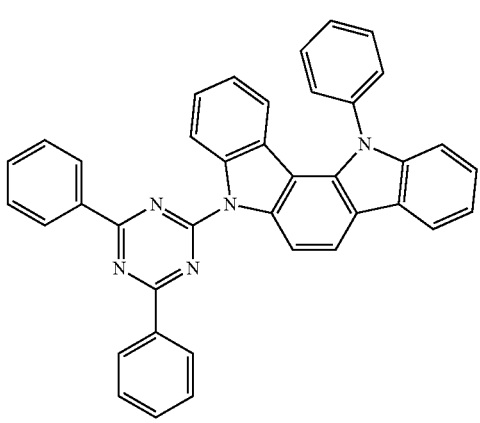
2-7
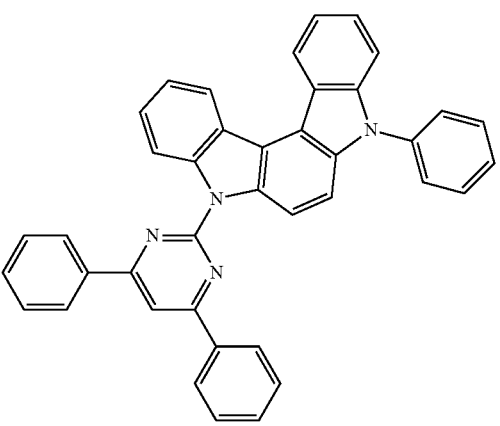
2-8
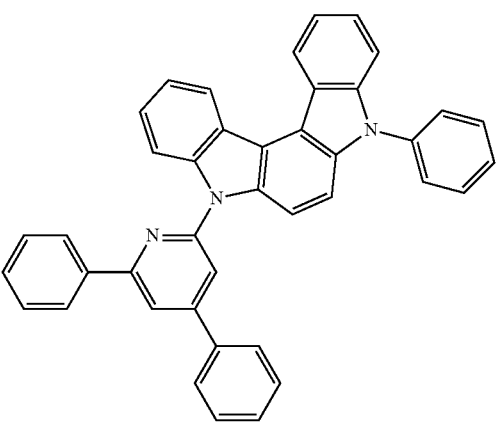
2-9
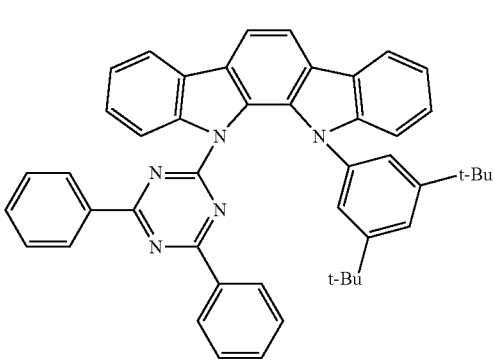
2-10
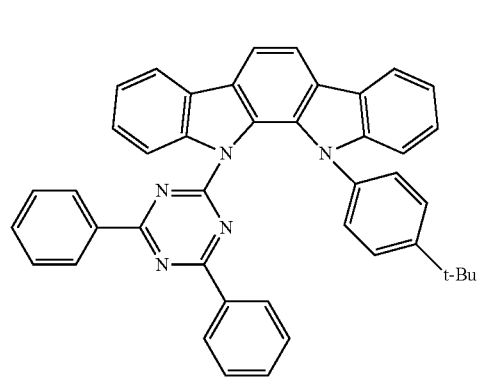

2-11
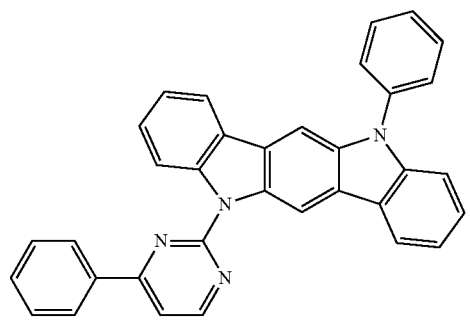
2-14
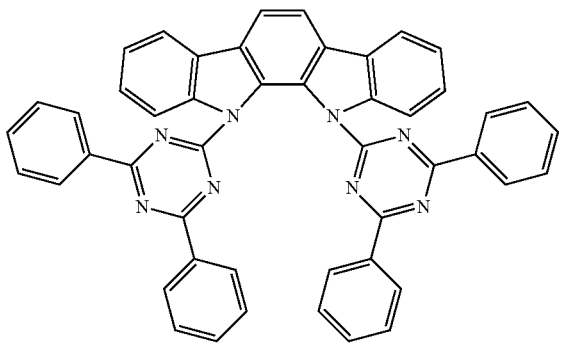
2-12
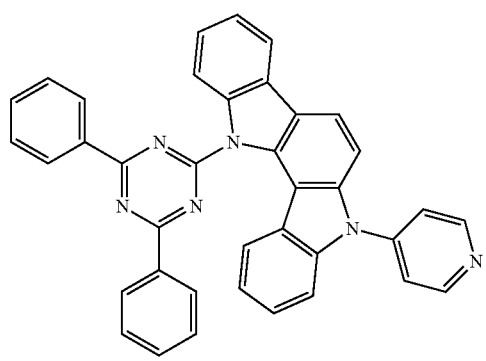
2-13
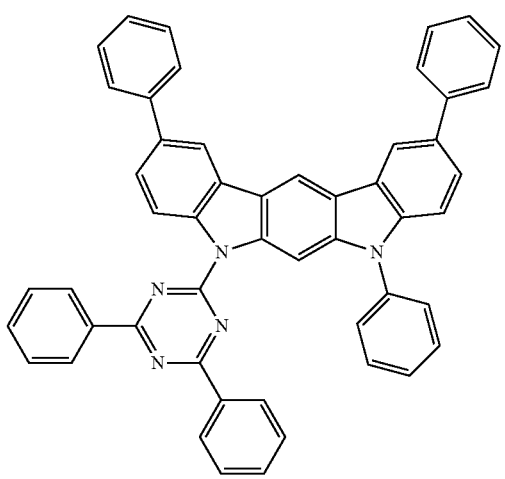
2-15
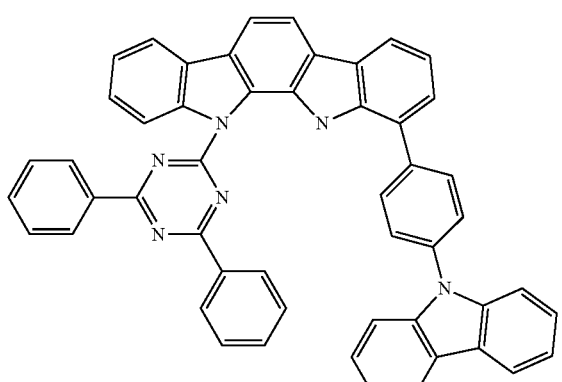
The compounds represented by formula (3) are illustrated below.
3-1
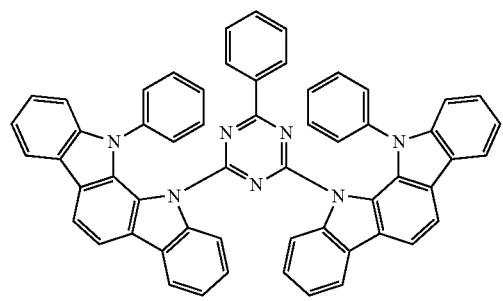
3-2
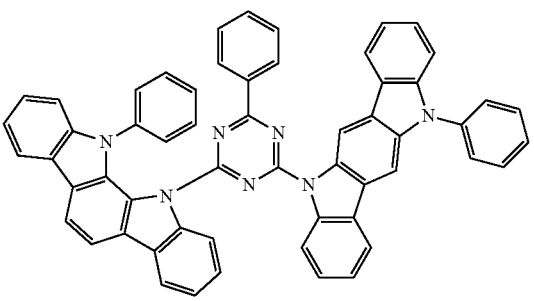

-continued
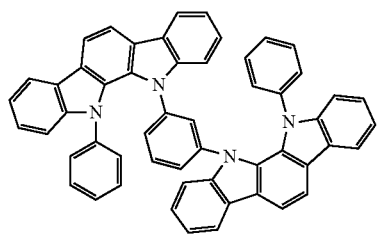
3-3
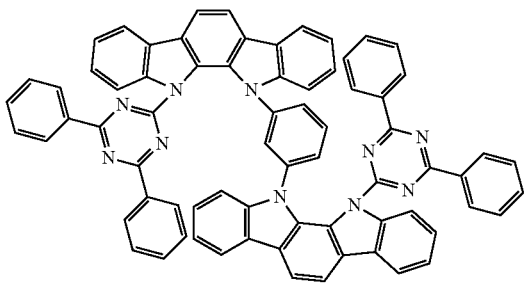
3-4
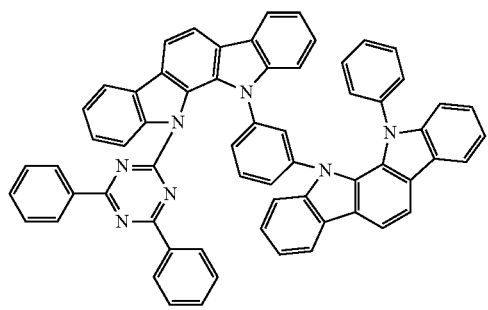
3-5
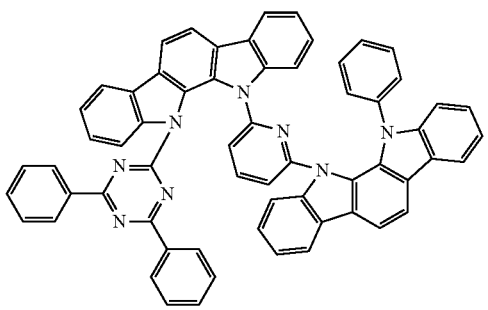
3-6
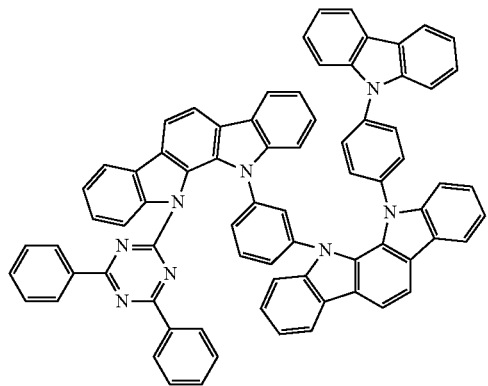
3-7
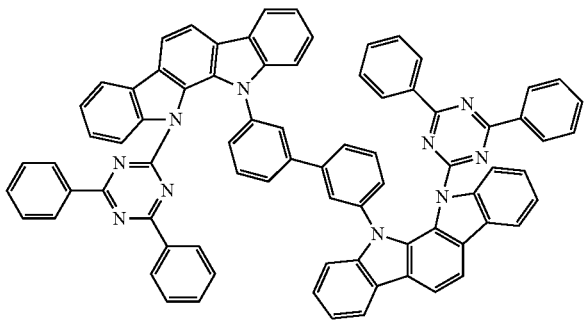
3-8
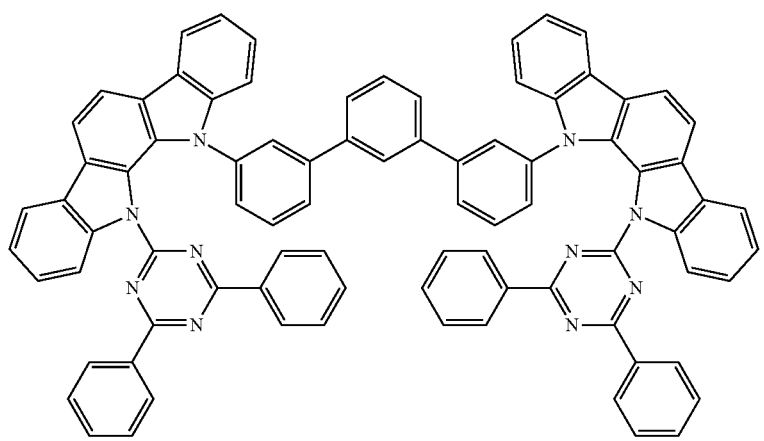
3-9

3-10
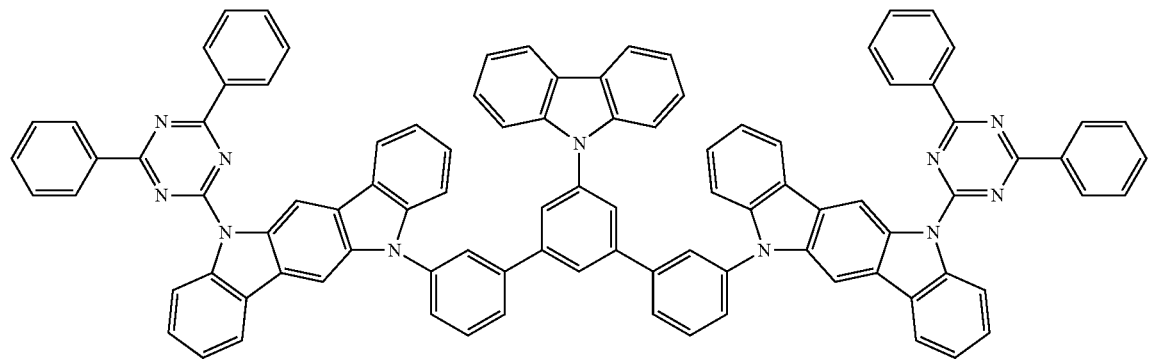
3-11
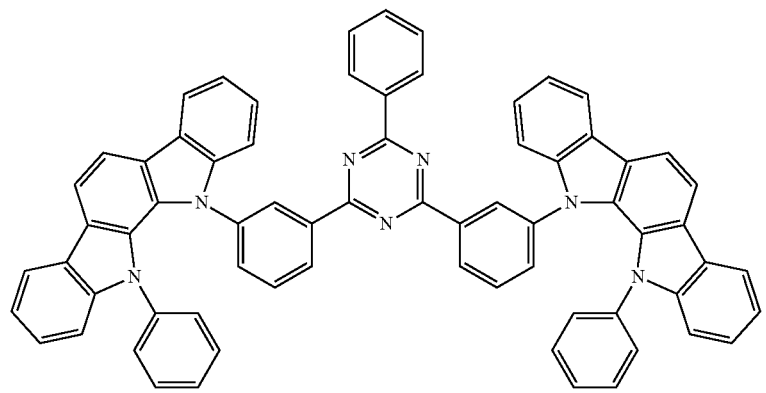
3-12
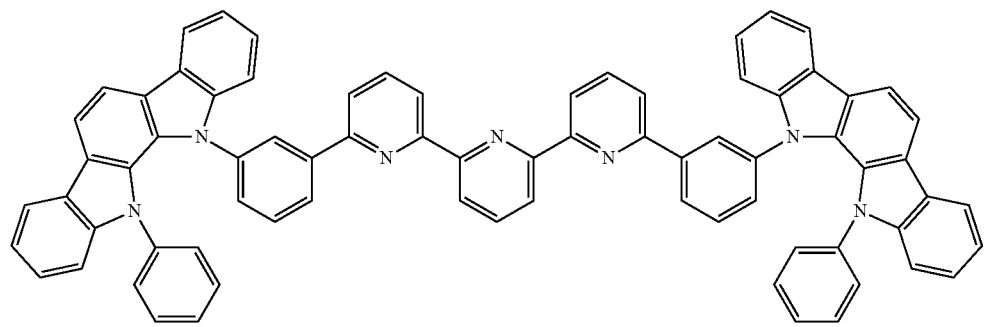
3-13
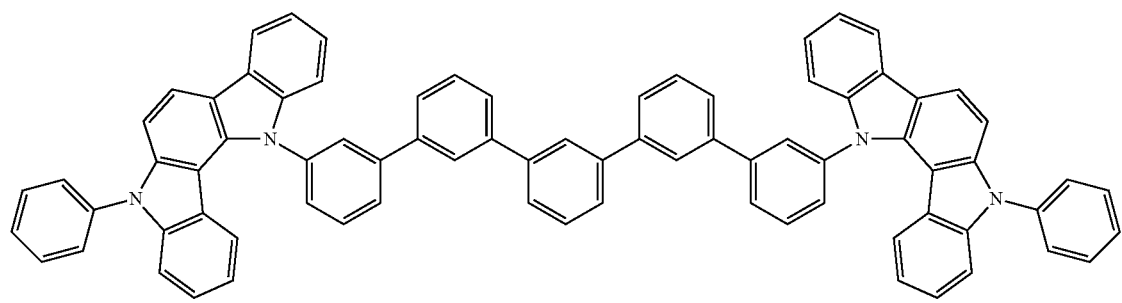

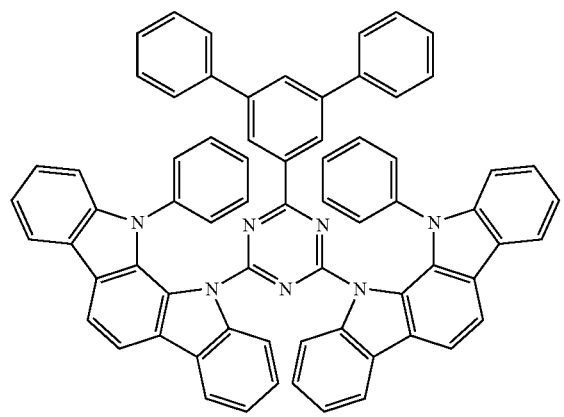

There are other compounds suitable for use as the first host material or the second host material in addition to those represented by formulas (1), (2), and (3); for example, 4,4'-N,N'-dicarbazolylbiphenyl (CBP) and 3-(4-tert-butylphenyl)-4-phenyl-5-(4-biphenylyl)-1,2,4-triazole (TAZ).

The first host material is selected at the start and the second host material is selected thereafter from the aforementioned compounds which can be used as host materials. Supposing that the values of IP, EA, and T1 of the first host material are respectively designated as IP (1), EA (1), and T1 (1) and those of the second host material as IP (2), EA (2), and T1 (2), a selection is made so as to control IP (1)-IP (2), EA (1)-EA (2), and T1 (1)-T1 (2) respectively within the range of ±0.10 eV. In order to satisfy all of these relationships simultaneously, a compound for the first host material and a compound for the second host material preferably have a similar skeleton. Moreover, the values of IP, EA, and T1 can be calculated on the basis of the molecular structure of the selected compounds as described earlier.

It is preferable to use two species selected from the compounds represented by formula (1) as the first host material and the second host material. It is more preferable to use two species selected from the compounds represented by formula (2) or (3) as the first host material and the second host material.

The light-emitting layer of an organic EL device in this invention comprises a host material and a phosphorescent dopant material and the host material comprises the first host material and the second host material.

The ratio of the first host material to the second host material on a weight basis is 90:10 to 10:90, preferably 75:25 to 25:75, more preferably 2:1 to 1:2. The content of the host material in the light-emitting layer is not limited specifically and it is preferably in the range of 50-99 wt %.

The phosphorescent dopant material is preferably a complex containing a noble metal element such as iridium, platinum, and ruthenium at the center, although there is no restriction on the color of emitted light and the molecular structure. The content of the phosphorescent dopant material in the light-emitting layer is in the range of 1-50 wt %, preferably in the range of 5-30 wt %, although it is not restricted specifically.

Examples of the phosphorescent dopant materials are shown below, but they are not limited thereto. The phosphorescent dopant selected for use is preferably the one that emits light with a maximum wavelength of not more than 580 nm.

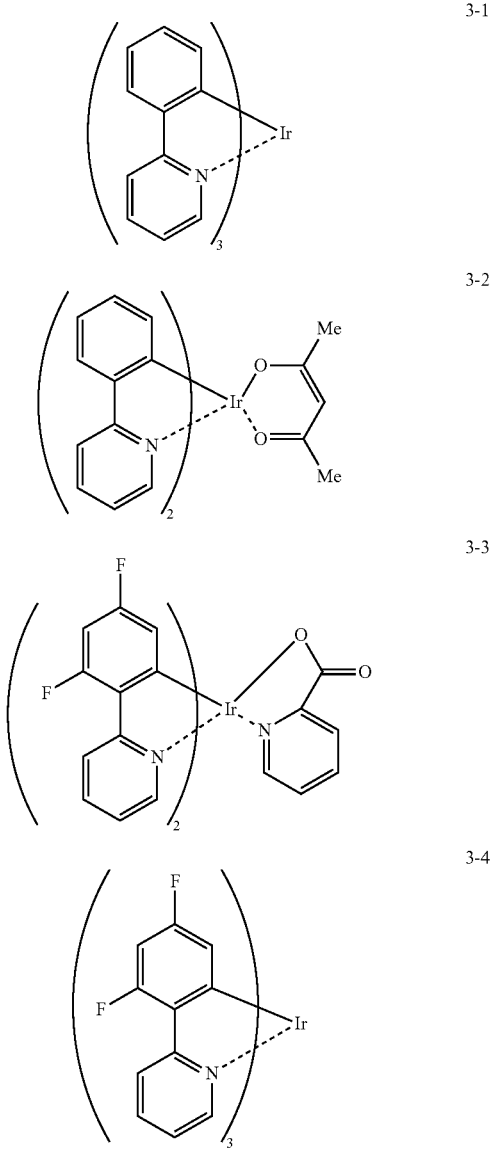

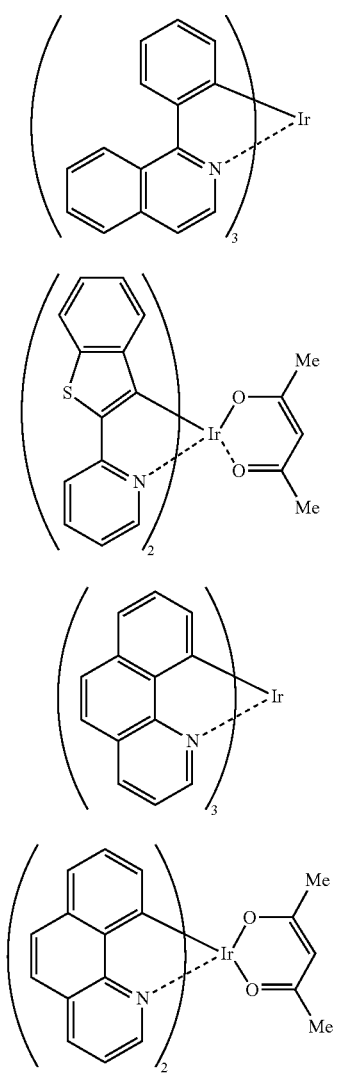

A wet process to be used in forming a film for the light-emitting layer is not restricted specifically and a selection may be made from wet processes such as spin coating, spray coating, dip coating, and doctor blade coating. The combined use of the first host material and the second host material is particularly effective for inhibiting crystallization of the host materials during the film-forming step by a wet process and enhances the luminous efficiency.

The wet process here refers to a process which consists of preparing a solution of an organic EL device material such as a host material in a solvent, applying the solution to a substrate or to an organic layer formed thereon, and drying the solution.

The solution is prepared, for example, by mixing an organic EL device material such as a host material and a solvent with stirring and a treatment such as heating and ultrasonic irradiation may be applied to accelerate dissolution of the material. The concentration of the solution is not limited specifically and it is preferably 0.01-50 wt %, more preferably 0.1-10 wt %. Further, a thickening agent, an anti-foaming agent, a surfactant, or the like may be added according to the need.

The film-forming process using the aforementioned coating solution is not limited specifically and a number of processes such as spin coating, slit coating, capillary coating, spray coating, ink jet coating, dip coating, and doctor blade coating are available. The drying method is not limited and, according to one method, a substrate is heated on a hot plate. The drying temperature varies with the solvent to be used and it is preferably 0-200° C., more preferably 50-150° C.

The solvent to be used in the preparation of a coating solution is not limited specifically as long as it can dissolve the materials for the constituents of the light-emitting layer or the first host material, the second host material, and the dopant material without leaving solid matters and a mixture of two species or more of solvents may be used. The solvent preferably has a melting point of 0° C. or below and a boiling point of 30° C. or above.

Examples of the solvents are given below, but they are not limited thereto: cyclohexane, carbon tetrachloride, tetrachloroethane, octylbenzene, dodecylbenzene, toluene, xylene, mesitylene, indane, methylnaphthalene, decalin, chlorobenzene, dichlorobenzene, N-methyl-2-pyrrolidinone (NMP), dimethylformamide (DMF), dimethylacetamide, diisopropyl ether, dibutyl ether, ethylene glycol, propylene glycol, triethylene glycol, diethylene glycol, glycerol, anisole, phenetole, tetrahydrofuran, 1,4-dioxane, 1,3-dioxolane, dibutyl ether, methyl alcohol, ethyl alcohol, n-propyl alcohol, isopropyl alcohol, n-butyl alcohol, sec-butyl alcohol, tert-butyl alcohol, isophorone, acetone, cyclohexanone, cyclopentanone, methyl ethyl ketone, methyl isobutyl ketone (MIBK), 2-heptanone, tetralone, chloroform, dichloromethane, dichloroethane, gamma-butyrolactone, ethyl acetate, diethyl carbonate, propylene carbonate, quinoline, pyridine, 4-ethylmorpholine, acetonitrile, butyronitrile, nitroethane, nitrobenzene, fluorobenzene, hexamethyldisiloxane, Butyl Cellosolve, carbon disulfide, terpineol, and ion-exchanged water (pure water).

The layers other than the light-emitting layer of an organic EL device in this invention will be explained below.

The substrate 1 is not limited specifically as long as it is one of substrates generally used in the fabrication of organic electroluminescent devices. However, it is preferable to use an organic substrate that is transparent, smooth on the surface, easy to handle, and waterproof, a transparent plastic substrate, or a glass substrate.

The anode 2 is not limited specifically as long as it is made from a material generally used in the fabrication of organic electroluminescent devices and it is preferably made from a metal or a metal oxide exhibiting excellent transparency and electrical conductivity. For example, indium tin oxide (ITO), indium zinc oxide (IZO), tin oxide ($SnO_2$), or zinc oxide (ZnO) can be used.

The hole-injecting layer 3 is formed on the anode as a thin film of an HIL material with a thickness of 5-500 nm. There is no specific restriction on the HIL material as long as it is one of materials generally used in the fabrication of organic electroluminescent devices; for example, an HIL material such as copper phthalocyanine (CuPc) and poly(3,4-ethylenedioxythiophene)poly(styrenesulfonate) (PEDOT/PSS) can be used. The film-forming process is not limited and it is possible to use not only a vapor deposition process, typically vacuum vapor deposition, but also a wet process such as spin coating, slit coating, capillary coating, spray coating, ink jet coating, dip coating, and doctor blade coating.

The hole-transporting layer 4 is formed on the hole-injecting layer as a thin film of an HTL material with a thickness of 5-500 nm. There is no specific restriction on the HTL material as long as it is one of materials generally used in the fabrication of organic electroluminescent devices; for example, an HTL material such as N,N'-bis(3-methylphenyl)-N,N'-diphenyl-1,1'-biphenyl-4,4'-diamine (TPD) and N,N'-di(naphthalen-1-yl)-N,N'-diphenyl-1,1'-biphenyl-4,4'-diamine (α-NPD) can be used. Likewise, a polymeric material such as polyvinylcarbazole (PVK) can be used. The film-forming process is not limited and it is possible to use not only a vapor deposition process, typically vacuum vapor deposition, but also a wet process such as spin coating, slit coating, capillary coating, spray coating, ink jet coating, dip coating, and doctor blade coating.

The electron-transporting layer 6 is formed on the light-emitting layer as a thin film of an ETL material with a thickness of 5-500 nm. There is no specific restriction on the ETL material as long as it is one of materials generally used in the fabrication of organic electroluminescent devices; for example, an HTL material such as 2-(4-biphenylyl)-5-(p-tert-butylphenyl)-1,3,4-oxadiazole (tBu-PBD), 2,9-dimethyl-4,7-diphenyl-1,10-phenanthroline (BCP), bathophenanthroline (Bphen), tris(8-hydroxyquinolinato)aluminum (Alq3), and bis(2-methyl-8-hydroxyquinolinato)(4-phenylphenolato)aluminum (BAlq) can be used. The film-forming process is not limited and it is possible to use not only a vapor deposition process, typically vacuum vapor deposition, but also a wet process such as spin coating, slit coating, capillary coating, spray coating, ink jet coating, dip coating, and doctor blade coating.

The cathode 7 is not specifically limited as long as it is made from a material generally used in the fabrication of organic electroluminescent devices. It is preferably made from a metallic material of excellent electrical conductivity; for example, a metal such as Al, Cs, and Er, an alloy such as an Mg—Ag alloy, an Al—Li alloy, an Al—Mg alloy, and a Cs—Te alloy, and a composite of layered structure such as Ca/Al, Mg/Al, Li/Al, Cs/Al, $Cs_2O$/Al, LiF/Al, and $ErF_3$/Al.

EXAMPLES

This invention will be explained concretely with reference to the examples below, but it will not be limited by the description in the examples unless the execution exceeds the substance of this invention.

Indolo[2,3-a]carbazole and 2-chloro-4,6-diphenyl-1,3,5-triazine to be used in the following Synthetic Examples 1-5 and Compound 2-1 to be used in Example 1 were synthesized in accordance with the procedures described in WO08-056746. Further, Compound 3-1 was synthesized in accordance with the procedure described in WO07-063754.

Synthetic Example 1

Synthesis of Compound 2-9

In a 1-liter four-necked flask under a nitrogen blanket were placed 28.53 g (111.4 mmol) of indolo[2,3-a]carbazole, 21.56 g (156.02 mmol) of potassium carbonate, 35.41 g (557.21 mmol) of copper powder, 30.00 g (111.4 mmol) of 1-bromo-3,5-di-tert-butylbenzene, and 450 g of tetraethylene glycol dimethyl ether and the mixture was heated at an inner temperature of 205° C. with stirring for 24 hours. The reaction mixture was cooled to room temperature, the solid was filtered off with a filter aid, and the filtrate was concentrated under reduced pressure and then fractionated and purified by a silica gel column to yield 7.42 g of a white solid. The FD-MS spectrum of the white solid has a peak of protonated molecular ion ($MH^+$) at m/z 445.

Then, 7.42 g (16.71 mmol) of the white solid and 150 g of dehydrated dimethylformamide were placed in a 300-ml recovery flask under a nitrogen blanket and 1.36 g of sodium hydride (58.8% dispersion in oil, 33.4 mmol) was thrown into the flask in several portions. After evolution of hydrogen subsided, a solution of 4.69 g (17.55 mmol) of 2-chloro-4,6-diphenyl-1,3,5-triazine in 50 g of dimethylformamide was added dropwise. Upon completion of the dropwise addition, the mixture was stirred at room temperature for 48 hours. The excess sodium hydride was quenched with distilled water. The reaction mixture was then added dropwise to 1,000 g of distilled water being vigorously stirred and the separated solid was collected by filtration. The solid was washed with methanol and dried overnight at 80° C. under reduced pressure to yield 6.29 g of a crude product. The crude product was purified by recrystallization to yield 3.36 g of a product in white crystals. A peak of molecular ion ($M^+$) was observed at m/z 675 in the FD-MS spectrum of the product and the product in white crystals was confirmed to be Compound 2-9.

Synthetic Example 2

Synthesis of Compound 2-10

In a 500-ml three-necked flask under a nitrogen blanket were placed 9.84 g (38.4 mmol) of indolo[2,3-a]carbazole, 15.94 g (115.33 mmol) of potassium carbonate, 12.22 g (192.22 mmol) of copper powder, 10.00 g (38.4 mmol) of 4-tert-butyliodobenzene, and 150 g of 1,3-dimethyl-2-imidazolidinone and the mixture was heated at an inner temperature of 205° C. with stirring for 20 hours. The reaction mixture was cooled to room temperature, the solid was filtered off with a filter aid, and the filtrate was concentrated under reduced pressure. The concentrated filtrate was transferred to a separatory funnel, 700 ml of ethyl acetate and 10% hydrochloric acid were added, the mixture was left standing for 0.5 hour, and the lower layer was discarded. The upper layer was washed with distilled water and then with a saturated aqueous sodium chloride solution, dried over magnesium sulfate, and stripped of the solvent by distillation under reduced pressure to yield a brown solid. The brown solid was purified by a silica gel column and recrystallized from dichloromethane/ethanol to yield 6.30 g of a product in white crystals. The FD-MS spectrum of the product has a peak of protonated molecular ion ($MH^+$) at m/z 389.

Then, 6.30 g (16.24 mmol) of the product in white crystals and 200 g of dehydrated dimethylformamide were placed in a 1-liter recovery flask under a nitrogen blanket and 0.72 g of sodium hydride (60.2% dispersion in oil, 17.86 mmol) was thrown into the flask in several portions. After evolution of hydrogen subsided, a solution of 4.78 g (17.86 mmol) of 2-chloro-4,6-diphenyl-1,3,5-triazine in 50 g of dimethylformamide was added dropwise. Upon completion of the dropwise addition, the mixture was stirred at room temperature for 72 hours. The excess sodium hydride was quenched with distilled water. The reaction mixture was then added dropwise to 260 g of distilled water being vigorously stirred and the separated solid was collected by filtration. The solid was washed by reslurrying in methanol at 50° C. for 3 hours and then dried overnight at 80° C. under reduced pressure to yield 8.39 of a crude product. The crude product was purified by recrystallization from dichloromethane to yield 3.31 g of a product in pale yellow crystals. A peak of protonated molecular ion ($MH^+$) was observed at m/z 620 in the FD-MS spectrum of the product and the product in pale yellow crystals was confirmed to be Compound 2-10.

Synthetic Example 3

Synthesis of Compound 3-4

In a 1-liter four-necked flask under a nitrogen blanket were placed 45.0 g (0.176 mol) of indolo[2,3-a]carbazole, 72.9 g (0.527 mol) of potassium carbonate, 55.9 g (0.879 mol) of copper powder, 29.0 g (0.088 mol) of 1,3-diiodobenzene, and 638 g of tetraethylene glycol dimethyl ether and the mixture was heated at an inner temperature of 205° C. with stirring for 18 hours. The reaction mixture was cooled to room temperature and the solid was filtered off with a filter aid. The filtrate was transferred to a separatory funnel, 1,400 g of 10 wt % hydrochloric acid was added, and the mixture was extracted with 2,100 g of ethyl acetate. The ethyl acetate layer was washed successively with distilled water and a saturated aqueous sodium chloride solution and dried over magnesium sulfate, the hydrated magnesium sulfate was removed by suction filtration, and the solvent was distilled off under reduced pressure. The residue was reslurried in dichloromethane and then in toluene and dried at 80° C. under reduced pressure to yield 29.08 g of a white solid. The FD-MS spectrum of the white solid has a peak of protonated molecular ion ($MH^+$) at m/z 587.

Then, 27.09 g (46.23 mmol) of the white solid and 600 g of dehydrated dimethylformamide were placed in a 1-liter four-necked flask under a nitrogen blanket and 7.40 g of sodium hydride (60.0% dispersion in oil, 0.185 mol) was thrown into the flask in several portions. After evolution of hydrogen subsided, a solution of 25.97 g (0.097 mol) of 2-chloro-4,6-diphenyl-1,3,5-triazine in 200 g of dimethylformamide was added dropwise. Upon completion of the dropwise addition, the mixture was stirred at room temperature for 20 hours. The excess sodium hydride was quenched with distilled water. Then, 400 g of distilled water was added and the separated solid was collected by filtration. The solid was recrystallized from toluene to yield 12.69 g of a product in pale yellow crystals. A peak of protonated molecular ion ($MH^+$) was observed at m/z 1049 in the FD-MS spectrum of the product and the product in pale yellow crystals was confirmed to be Compound 3-4.

Synthetic Example 5

Synthesis of Compound 3-9

In a 2-l four-necked flask under a nitrogen blanket were placed 36.96 g (0.112 mol) of 1,3-diiodobenzene, 45.00 g (0.224 mol) of 3-bromophenylboronic acid, 4.27 g (3.7 mmol) of tetrakis(triphenylphosphine)palladium(0), 225 ml of ethanol, and 603 ml of toluene were placed and the mixture was stirred at room temperature. To this solution were added 142.2 g (1.342 mol) of sodium carbonate and 297 g of distilled water and the mixture was heated at an inner temperature of 75° C. with stirring for 19 hours. The mixture was cooled to room temperature, the aqueous layer was withdrawn, the organic layer was washed with a saturated aqueous sodium chloride solution and dried over magnesium sulfate, the hydrated magnesium sulfate was removed by suction filtration, and the solvent was distilled off under reduced pressure. The residue was purified by a silica gel column to yield 42.13 g of a brown oil. The brown oil was purified by distillation under a reduced pressure of 0.2 kPa and a fraction distilling in the range of 220-234° C. was obtained as a colorless oil weighing 21.55 g. Three peaks of molecular ions ($M^+$) were observed respectively at m/z 386, 388, and 390 at an intensity ratio of 1:2:1 in the FD-MS spectrum of the colorless oil and the product was confirmed to be 1,3-bis(3-bromophenyl)benzene.

Then, 20.0 g (78.1 mmol) of indolo[2,3-a]carbazole, 31.11 g (225.1 mmol) of potassium carbonate, 24.85 g (391.0 mmol) of copper powder, 15.21 g (39.2 mmol) of 1,3-bis(3-bromophenyl)benzene, and 300 g of 1,3-dimethyl-2-imidazolidinone were placed in a 500-ml three-necked flask under a nitrogen blanket and the mixture was heated at an inner temperature of 210° C. with stirring for 23 hours. The reaction mixture was cooled to room temperature and the solid was filtered off with a filter aid. The filtrate was transferred to a separatory funnel, 1,000 ml of 10 wt % hydrochloric acid was added, and the mixture was extracted with 700 g of ethyl acetate. The ethyl acetate layer was washed with a saturated aqueous sodium chloride solution and dried over magnesium sulfate, the hydrated magnesium sulfate was removed by suction filtration, and the solvent was distilled off under reduced pressure. The residue was washed by reslurrying in dichloromethane and dried at 80° C. under reduced pressure to yield 13.24 g of a white solid. The FD-MS spectrum of the white solid has a peak of molecular ion ($MH^+$) at m/z 738.

Then, 13.15 g (17.82 mmol) of the aforementioned white solid and 280 g of 1,3-dimethyl-2-imidazolidinone were placed in a 1-liter four-necked flask under a nitrogen blanket and 2.84 g of sodium hydride (60.2% dispersion in oil, 71.28 mmol) was thrown into the flask in several portions. After evolution of hydrogen subsided, a solution of 11.92 g (44.56 mmol) of 2-chloro-4,6-diphenyl-1,3,5-triazine in 60 g of 1,3-dimethyl-2-imidazolidinone was added dropwise. Upon completion of the dropwise addition, the mixture was stirred at room temperature for 20 hours. The excess sodium hydride was quenched with distilled water. The reaction mixture was transferred to a separatory funnel, 700 g of distilled water was added, and the mixture was extracted with 700 g of ethyl acetate. The ethyl acetate layer was washed twice with 700 g of distilled water and dried over magnesium sulfate, the hydrated magnesium sulfate was removed by suction filtration, and the solvent was distilled off under reduced pressure. The residue was purified by a silica gel column and then dried overnight at 80° C. under reduced pressure to yield 10.72 g of an amorphous white solid. The solid was purified by recrystallization from tetrahydrofuran/acetonitrile to yield 3.16 g of a product in pale yellow crystals. A peak of protonated molecular ion ($MH^+$) was observed at m/z 1201 in the FD-MS spectrum of the product and the product in pale yellow crystals was confirmed to be Compound 3-9.

Synthetic Example 6

Synthesis of Compound 3-14

Compound 3-14 was synthesized in accordance with the procedure described for the synthesis of Compound 3-1 in WO07-063754 except that (3,5-diphenyl)phenylboronic acid was substituted for phenylboronic acid. A peak of molecular ion (M+) was observed at m/z 970 in the FD-MS spectrum of the product thus synthesized and the product was confirmed to be Compound 3-14.

Synthetic Example 7

Synthesis of Compound A

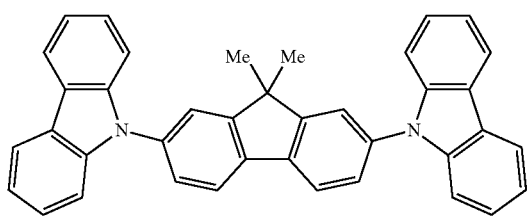

(A)

Compound A was synthesized in accordance with the procedure described in JP2005-239703 A. A peak of molecular ion (M+) was observed at m/z 524 in the FD-MS spectrum of the product thus synthesized and the product was confirmed to be Compound A.

Synthetic Example 8

Synthesis of Compound B

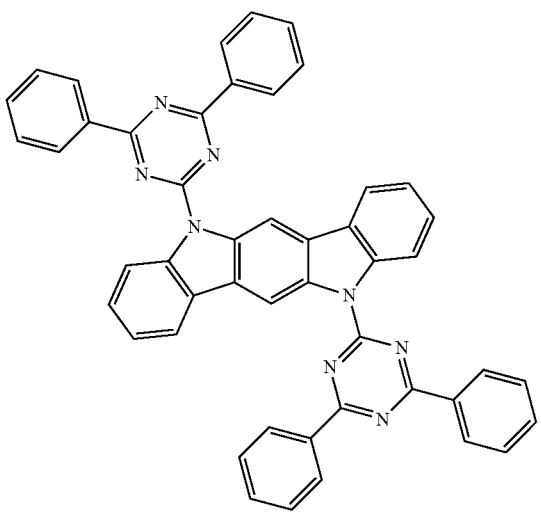

(B)

Compound B was synthesized in accordance with the procedure described in Example 4 of WO08-056746 A.

Synthetic Example 9

Synthesis of Compound C

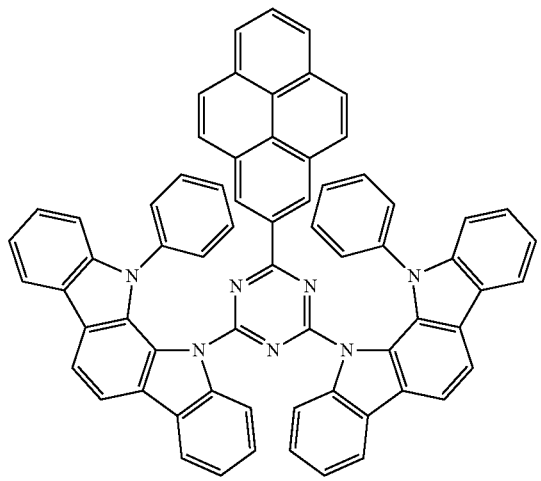

(C)

Compound C was synthesized in accordance with the procedure described for Compound 3-1 in WO07-063754 except that pyren-2-ylboronic acid was substituted for phenylboronic acid. A peak of molecular ion (M+) was observed at m/z 941 in the FD-MS spectrum of the product thus synthesized and the product was confirmed to be Compound C.

Reference Example 1

The values of IP, EA, and T1 were calculated for Compounds 2-9, 2-10, 3-4, 3-9, 3-14, 2-1, 3-1, A, and B obtained in the aforementioned Synthetic Examples.

The values of IP, EA, and T1 were calculated by density functional theory (DFT) structure optimization using the molecular orbital program Gaussian 03, rev. CO2. The values of IP and EA were respectively the negatives (in terms of eV unit) of the HOMO energy and the LUMO energy calculated by structure optimization on the B3LYP/6-31G* level. In calculating the value of T1, structure optimization calculation was performed on the B3LYP/6-31G* and then the lowest triplet excitation energy was calculated on the TD-B3LYP/6-31G* level on the basis of the optimized structure. The values of IP, EA, and T1 are shown for each of the compounds in Table 1.

TABLE 1

| Compound | T1 | IP | EA |
|---|---|---|---|
| 2-1 | 2.78 | 5.26 | 1.87 |
| 2-9 | 2.74 | 5.22 | 1.88 |
| 2-10 | 2.74 | 5.21 | 1.87 |
| 3-1 | 2.81 | 5.28 | 1.80 |
| 3-4 | 2.79 | 5.35 | 1.87 |
| 3-9 | 2.79 | 5.25 | 1.92 |
| 3-14 | 2.79 | 5.29 | 1.82 |
| A | 2.78 | 5.24 | 1.29 |
| B | 2.75 | 5.46 | 1.90 |
| C | 2.12 | 5.28 | 1.85 |

Example 1 (Comparative)

An organic EL device having a structure similar to the one illustrated in FIG. 1 was fabricated with omission of the hole-transporting layer and addition of an electron-injecting layer. A glass substrate coated with a 150 nm-thick ITO anode was precleaned by UV/ozone cleaning and dried and a hole-injecting layer was formed by applying a 20 wt % ethanol solution of PEDOT/PSS (Baytron P CH8000) to the ITO anode by spin coating at 3,000 rpm for 60 seconds and drying the solution at 200° C. for 60 minutes. The thickness of the film at this time was 25 nm. Then, a light-emitting layer was formed by applying a solution of 38.0 parts by weight of Compound 2-1 as a host material and 2.0 parts by weight of tris(2-phenylpyridine)iridium (Ir(ppy)3) as a phosphorescent dopant material in 2,840 parts by weight of dichloromethane by spin coating at 4,000 rpm for 30 seconds and drying the solution at 120° C. for 30 minutes. The thickness of the light-emitting layer at this time was 70 nm. Then, an electron-transporting layer was formed by depositing tris(8-hydroxyquinolinato)aluminum (Alq3) by the vacuum vapor deposition method at a rate of 0.1 nm/sec to a thickness of 35 nm. Further, an electron-injecting layer was formed by depositing lithium fluoride (LiF) by the vacuum vapor deposition process to a thickness of 0.5 nm. Finally, an electrode was formed on the electron-injecting layer by depositing aluminum (Al) by the vacuum vapor deposition process to a thickness of 170 nm.

To evaluate the initial characteristics of the organic EL device thus fabricated, the current efficiency (cd/A) was measured by connecting the device to an outside power source and applying direct current voltage to the device so as to generate a current of 100 mA/cm$^2$. Further, as the lifetime characteristics of the device, the time until the initial luminance is reduced by half or the luminance half-life was measured by applying direct current voltage to the device so as to generate a constant current of 20 mA/cm$^2$, and expressing the results in terms of the case wherein the initial luminance is 1,000 cd/m$^2$. The current efficiency was 5.7 cd/A and the luminance half-life was 32 hours.

Example 2

An organic EL device was fabricated and evaluated as in Example 1 except 17.3 parts by weight of Compound 2-1 as the first host material and 20.7 parts by weight of Compound 2-9 as the second host material were used as the host material and the thickness of the light-emitting layer was 70 nm.

Example 3

An organic EL device was fabricated and evaluated as in Example 2 except that 18.0 parts by weight of Compound 2-1 was used as the first host material, 20.0 parts by weight of Compound 2-10 was used as the second host material, and the thickness of the light-emitting layer was 70 nm.

Example 4

An organic EL device was fabricated and evaluated as in Example 2 except that 13.3 parts by weight of Compound 2-1 was used as the first host material, 24.7 parts by weight of Compound 3-4 was used as the second host material, and the thickness of the light-emitting layer was 70 nm.

Example 5

An organic EL device was fabricated and evaluated as in Example 2 except that 12.1 parts by weight of Compound 2-1 was used as the first host material, 25.9 parts by weight of Compound 3-9 was used as the second host material, and the thickness of the light-emitting layer was 70 nm.

Example 6

An organic EL device was fabricated and evaluated as in Example 2 except that 23.6 parts by weight of Compound 2-1 was used as the first host material, 14.4 parts by weight of Compound 3-4 was used as the second host material, and the thickness of the light-emitting layer was 70 nm.

Example 7 (Comparative)

An organic EL device was fabricated and evaluated as in Example 2 except that 19.7 parts by weight of Compound 2-1 was used as the first host material, 18.3 parts by weight of Compound A was used as the second host material, and the thickness of the light-emitting layer was 70 nm.

Example 8 (Comparative)

An organic EL device was fabricated and evaluated as in Example 2 except that 16.7 parts by weight of Compound 2-1 was used as the first host material, 21.3 parts by weight of Compound B was used as the second host material, and the thickness of the light-emitting layer was 70 nm.

Example 9 (Comparative)

An organic EL device was fabricated and evaluated as in Example 2 except that 14.2 parts by weight of Compound 2-1 was used as the first host material, 23.8 parts by weight of Compound C was used as the second host material, and the thickness of the light-emitting layer was 70 nm.

Example 10 (Comparative)

An organic EL device was fabricated and evaluated as in Example 1 except that Compound 3-1 was used as the host material and the thickness of the light-emitting layer was 70 nm. The current efficiency was 10.8 cd/A and the luminance half-life was 48 hours.

Example 11

An organic EL device was fabricated and evaluated as in Example 2 except that 16.6 parts by weight of Compound 3-1 was used as the first host material, 21.4 parts by weight of Compound 3-4 was used as the second host material, and the thickness of the light-emitting layer was 70 nm.

Example 12

An organic EL device was fabricated and evaluated as in Example 2 except that 20.8 parts by weight of Compound 3-1 was used as the first host material, 17.2 parts by weight of Compound 2-9 was used as the second host material, and the thickness of the light-emitting layer was 70 nm.

Example 13

An organic EL device was fabricated and evaluated as in Example 2 except that 17.4 parts by weight of Compound 3-1 was used as the first host material, 20.6 parts by weight of Compound 3-14 was used as the second host material, and the thickness of the light-emitting layer was 70 nm.

Example 14 (Comparative)

An organic EL device was fabricated and evaluated as in Example 2 except that 14.8 parts by weight of Compound 3-1 was used as the first host material, 23.2 parts by weight of Compound A was used as the second host material, and the thickness of the light-emitting layer was 70 nm.

Example 15 (Comparative)

An organic EL device was fabricated and evaluated as in Example 2 except that 20.2 parts by weight of Compound 3-1 was used as the first host material, 17.8 parts by weight of Compound B was used as the second host material, and the thickness of the light-emitting layer was 70 nm.

Example 16 (Comparative)

An organic EL device was fabricated and evaluated as in Example 2 except that 17.7 parts by weight of Compound 3-1 was used as the first host material, 20.3 parts by weight of Compound C was used as the second host material, and the thickness of the light-emitting layer was 70 nm.

The results of Examples 1-6 are shown in Table 2. The results for the current efficiency and the luminance half-life are expressed in values relative to those of Example 1 which are taken as 100. In Table 2, H1 stands for the first host material and H2 for the second host material.

TABLE 2

| Example | H1 Compd. | H2 Compd. | Difference T1 | Difference IP | Difference EA | H1/H2 Ratio by weight | Current efficiency | Luminance half-life |
|---|---|---|---|---|---|---|---|---|
| 1 | 2-1 | — | — | — | — | 100/0 | 100 | 100 |
| 2 | 2-1 | 2-9 | −0.04 | −0.04 | +0.01 | 46/54 | 107 | 420 |
| 3 | 2-1 | 2-10 | −0.04 | −0.05 | 0 | 47/53 | 104 | 184 |
| 4 | 2-1 | 3-4 | +0.01 | +0.09 | 0 | 35/65 | 108 | 540 |
| 5 | 2-1 | 3-9 | +0.01 | −0.01 | +0.05 | 32/68 | 104 | 622 |
| 6 | 2-1 | 3-4 | +0.01 | +0.09 | 0 | 62/38 | 181 | 1284 |
| 7 | 2-1 | A | 0 | −0.02 | 0.58 | 52/48 | 102 | 96 |
| 8 | 2-1 | B | −0.03 | +0.20 | −0.03 | 44/56 | 95 | 50 |
| 9 | 2-1 | C | −0.66 | +0.02 | +0.02 | 37/63 | 35 | 77 |

The results of Examples 10-16 are shown in Table 3. The results for the current efficiency and the luminance half-life are expressed in values relative to those of Example 10 which are taken as 100. In Table 3, H1 stands for the first host material and H2 for the second host material.

TABLE 3

| Example | H1 Compd. | H2 Compd. | Difference T1 | Difference IP | Difference EA | H1/H2 Ratio by weight | Current efficiency | Luminance half-life |
|---|---|---|---|---|---|---|---|---|
| 10 | 3-1 | — | — | — | — | 100/0 | 100 | 100 |
| 11 | 3-1 | 3-4 | −0.02 | +0.07 | +0.07 | 44/56 | 151 | 455 |
| 12 | 3-1 | 2-9 | −0.07 | +0.06 | +0.08 | 55/45 | 120 | 216 |
| 13 | 3-1 | 3-14 | −0.02 | +0.01 | +0.02 | 46/54 | 106 | 177 |
| 14 | 3-1 | A | −0.03 | +0.04 | −0.51 | 39/61 | 86 | 85 |
| 15 | 3-1 | B | −0.06 | +0.18 | +0.10 | 53/47 | 89 | 61 |
| 16 | 3-1 | C | −0.69 | 0 | +0.05 | 47/53 | 33 | 78 |

INDUSTRIAL APPLICABILITY

According to this invention, it is possible to offer a highly reliable organic electroluminescent device by inhibiting crystallization of materials caused by feeble heat generated during the operation of the device while maintaining a balance of injection of electrons and holes and an efficient mechanism of phosphorescence. In particular, in the case where a film for the light-emitting layer is formed by a wet process, inhibition of crystallization in the drying step of the film makes it possible to offer an organic electroluminescent device of high luminance and high reliability. The organic EL device of this invention can maintain good luminous characteristics over a prolonged period of time.

The invention claimed is:

1. An organic electroluminescent device containing a light-emitting layer formed by a wet film-forming process between an anode and a cathode wherein the light-emitting layer comprises a phosphorescent dopant material and a host material having a molecular weight of not more than 10,000, the said host material is composed of a first host material and a second host material that is different from the first host material, the first host material or the second host material is a heterocyclic compound represented by the following formula (1), the ratio by weight of the first host material to the second host material is 90:10 to 10:90, and the first host material differs from the second host material by less than 0.1 eV in the ionization potential (IP), by less than 0.1 eV in the electron affinity (EA), and by less than 0.1 eV in the triplet energy (T1);

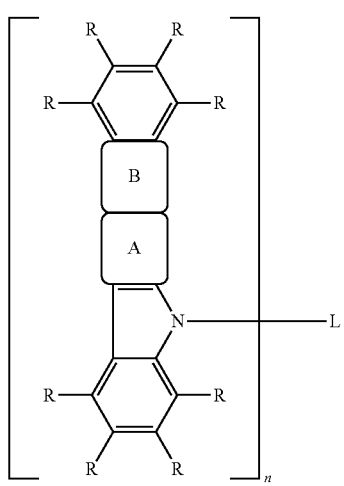

(1)

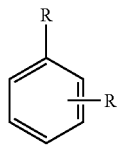

(1a)

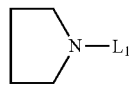

(1b)

wherein in formula (1):
ring A is an aromatic ring represented by formula (1a) and is fused to the adjacent rings at arbitrary positions and ring B is a heterocycle represented by formula (1b) and is fused to the adjacent rings at arbitrary positions;
R in formulas (1) and (1a) is independently hydrogen or a monovalent substituent and the adjacent substituents optionally together form a ring;
$L_1$ in formula (1b) is independently an aromatic hydrocarbon group or an aromatic heterocyclic group;
L is an n-valent aromatic hydrocarbon group or an n-valent aromatic heterocyclic group;
n is 1-4; and
when n is 2 or more, the fused heterocycle containing rings A and B are identical with or different from one another.

2. The organic electroluminescent device as described in claim 1, wherein the first host material and the second host material are heterocyclic compounds represented by formula (1).

3. The organic electroluminescent device as described in claim 1, wherein the ratio by weight of the first host material to the second host material is 75:25 to 25:75.

4. The organic electroluminescent device as described in claim 1, wherein the first host material or the second host material is a heterocyclic compound represented by the following formula (2) or (3);

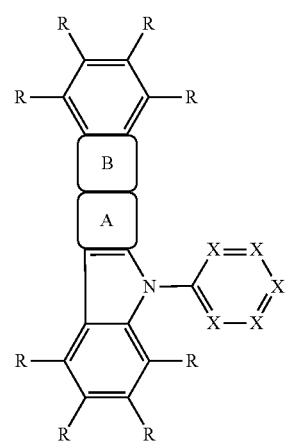

(2)

wherein in formula (2), ring A, ring B, and R respectively have the same meaning as in formula (1); X is independently C—H, N, or C-$L_2$ and $L_2$ is independently an aromatic hydrocarbon group or an aromatic heterocyclic group;

(3)

wherein in formula (3), ring A, ring B, and R respectively have the same meaning as in formula (1); Ar is independently a phenylene group or a divalent aromatic heterocyclic group; m is 1-5.

5. The organic electroluminescent device as described in claim 4 wherein the first host material and the second host materials are two species of heterocyclic compounds selected from the heterocyclic compounds represented by formula (2) or (3).

6. A method for fabricating an organic electroluminescent device wherein organic layers containing a light-emitting layer are disposed between an anode and a cathode and the light-emitting layer comprises a phosphorescent dopant material and a host material having a molecular weight of not more than 10,000, which comprises a step where the host material and the phosphorescent dopant material are prepared, the said host material being characterized in that it is composed of a first host material and a second host material that is different from the first host material, the first host material or the second host material is a heterocyclic compound represented by formula (1),
the ratio by weight of the first host material to the second host material is 90:10 to 10:90, and the first host material differs from the second host material by less than 0.1 eV in the ionization potential (IP), by less than 0.1 eV in the electron affinity (EA), and by less than 0.1 eV in the triplet energy (T1), a step where the host material and the phosphorescent dopant material are dissolved in a solvent to form a coating solution, and a step where the coating solution is applied to an organic layer adjacent to the light-emitting layer and dried;

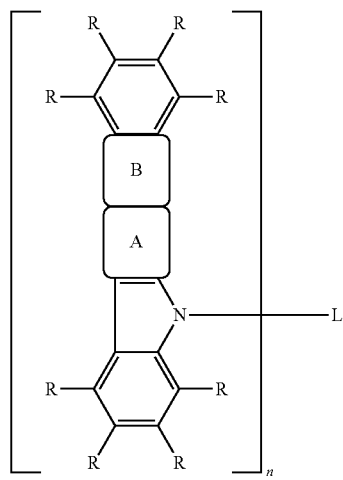
(1)

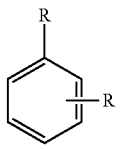
(1a)

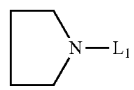
(1b)

wherein in formula (1):

ring A is an aromatic ring represented by formula (1a) and is fused to the adjacent rings at arbitrary positions and ring B is a heterocycle represented by formula (1b) and is fused to the adjacent rings at arbitrary positions;

R in formulas (1) and (1a) is independently hydrogen or a monovalent substituent and the adjacent substituents optionally together form a ring;

$L_1$ in formula (1b) is independently an aromatic hydrocarbon group or an aromatic heterocyclic group;

L is an n-valent aromatic hydrocarbon group or an n-valent aromatic heterocyclic group;

n is 1-4; and when n is 2 or more, the fused heterocycle containing rings A and B are identical with or different from one another.

\* \* \* \* \*